US00PP16843P2

(12) United States Plant Patent
Pieters

(10) Patent No.: US PP16,843 P2
(45) Date of Patent: Jul. 18, 2006

(54) ***CHRYSANTHEMUM* PLANT NAMED 'GEDI THREE MIL'**

(50) Latin Name: *Chrysanthemum morifolium*
Varietal Denomination: Gedi Three Mil

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 11/118,273

(22) Filed: Apr. 28, 2005

(51) Int. Cl.
*A01H 5/00* (2006.01)

(52) U.S. Cl. ..... Plt./288

(58) Field of Classification Search ..... Plt./288
See application file for complete search history.

(56) References Cited

U.S. PATENT DOCUMENTS

PP13,102 P2 10/2002 Pieters
PP13,689 P2 4/2003 Pieters
PP13,885 P2 6/2003 Pieters

*Primary Examiner*—Kent Bell
*Assistant Examiner*—Annette H Para
(74) *Attorney, Agent, or Firm*—Knobbe, Martens, Olson & Bear, LLP

(57) ABSTRACT

A new and distinct *Chrysanthemum* plant cultivar is disclosed, characterized by white, decorative flowers that naturally bloom in early September. The plant is moderately vigorous, and has a round, slightly spreading growth habit.

1 Drawing Sheet

Figure 1:
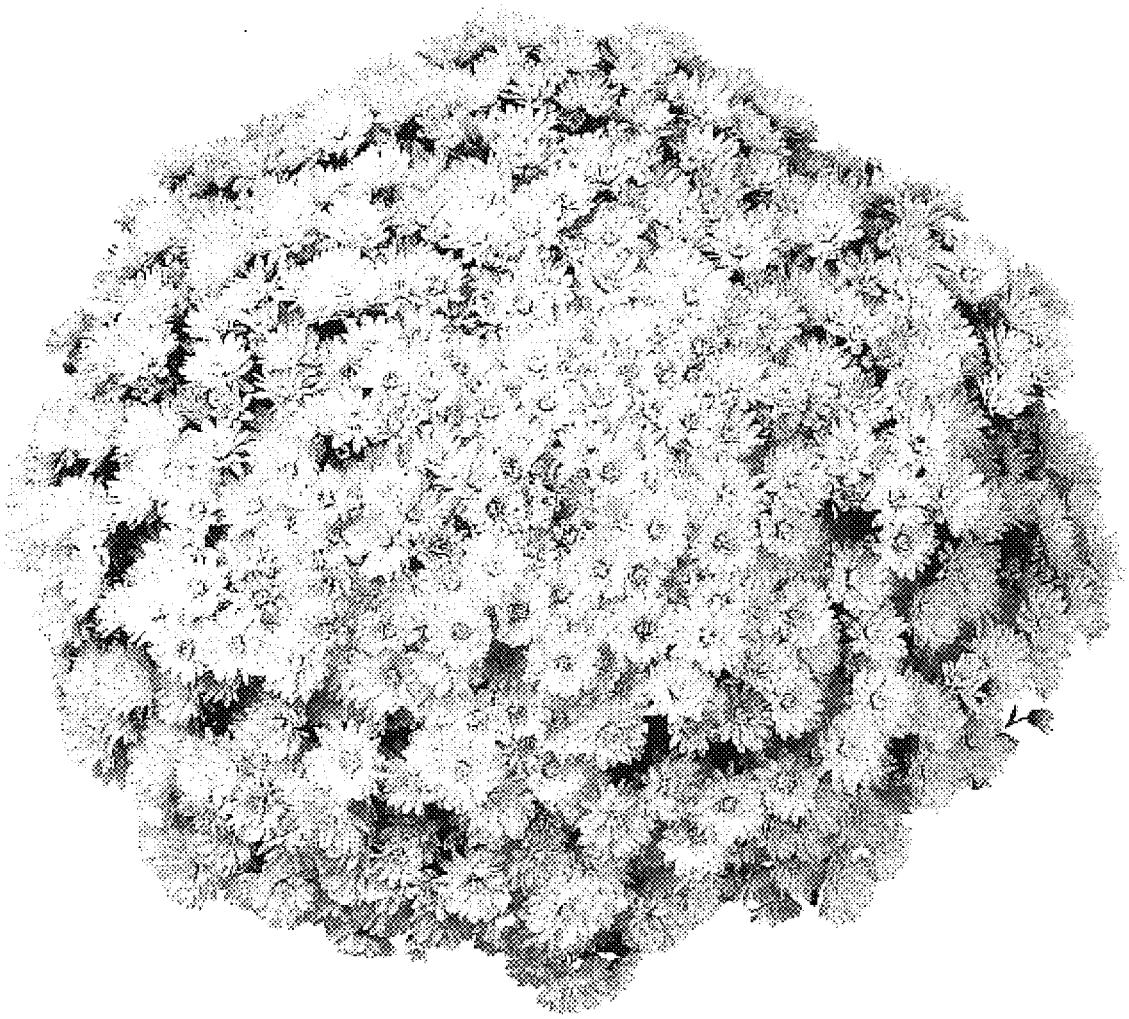

Latin name of the genus and species: *Chrysanthemum morifolium.*
Variety denomination: 'Gedi Three Mil'.

BACKGROUND OF THE INVENTION

The new cultivar 'Gedi Three Mil' is a product of hybridization of a female parent *Chrysanthemum* plant variety 'Gedi One Tar' (U.S. Plant Pat. No. 13,689) and a male parent *Chrysanthemum* plant variety 'Gedi One Ter' (U.S. Plant Pat. No. 13,885) in a controlled environment. The new cultivar 'Gedi Three Mil' was discovered and selected by Dirk Pieters in Oostniewkerke, Belgium in September 1998.

Asexual reproduction of the new cultivar 'Gedi Three Mil' by terminal cuttings and tissue culture was performed in a controlled environment in Oxnard, Calif., and has shown that the unique features of this cultivar are stable and reproduced true to type on successive generations.

SUMMARY OF THE INVENTION

The cultivar 'Gedi Three Mil' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Gedi Three Mil'. These characteristics in combination distinguish 'Gedi Three Mil' as a new and distinct *Chrysanthemum* cultivar:

1. White, decorative flowers.
2. Round, slightly spreading growth habit.
3. Moderate plant vigor.
4. The plant naturally blooms in early September.

Plants of the new cultivar 'Gedi Three Mil' are similar to plants of the female parent variety, 'Gedi One Tar,' in most horticultural characteristics, however the ray florets of the new cultivar are white, in comparison to the light-yellow colored ray florets of the female parent variety 'Gedi One Tar.' Additionally, the new variety 'Gedi Three Mil' is taller and has a more spreading growth habit than the female parent variety 'Gedi One Tar.'

Plants of the new cultivar 'Gedi Three Mil' are similar to plants of the male parent variety, 'Gedi One Ter' in most horticultural characteristics, however plants of the new cultivar 'Gedi Three Mil' have more flowers per flowering branch, and significantly fewer ray florets than plants of the male parent variety 'Gedi One Ter.' Additionally, the new variety 'Gedi Three Mil' is taller and wider than the male parent variety 'Gedi One Ter.'

In comparison to the commercially available variety 'Florence' (U.S. Plant Pat. No. 13,102), 'Gedi Three Mil' has a larger diameter flower which blooms about five days earlier than the comparable variety. Additionally, the new variety 'Gedi Three Mil' has about 13 more flowers per flowering branch in comparison to the comparable variety 'Florence.'

BRIEF DESCRIPTION OF THE PHOTOGRAPH

The accompanying photograph in FIG. 1 illustrates in full color a typical plant of 'Gedi Three Mil' grown in a 2 gallon container. One cutting was used in the pot. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'Gedi Three Mil' plants grown in Oxnard, Calif., during the month of September 2003. The growing temperature ranged from about 12° C. to 15° C. at night to about 12° C. to 20°

C. during the day. Measurements and numerical values represent averages of typical flowering types, and are believed to apply to plants of the variety grown under similar conditions of soil and climate elsewhere:

Botanical classification: *Chrysanthemum morifolium* 'Gedi Three Mil.'
Commercial classification: Garden-type *Chrysanthemum*.

PROPAGATION

Time to rooting: 7 to 14 days at approximately 21° C.
Root description: Fine, fibrous.

PLANT

Growth habit: Mounding herbaceous perennial.
Height: Approximately 28.5 cm.
Plant spread: Approximately 31 cm.
Growth rate: Moderate.
Branching characteristics: Free branching.
Length of lateral branches: Approximately 22 cm.
Number of leaves per lateral branch: Approximately 18.
Age of plant described: Approximately 145 days from a rooted cutting.

FOLIAGE

Leaf:
*Arrangement.*—Alternate.
*Average length.*—Approximately 6.4 cm.
*Average width.*—Approximately 5.8 cm.
*Shape of blade.*—Ovate.
*Apex.*—Cuspidate.
*Base.*—Attenuate.
*Attachment.*—Stalked.
*Margin.*—Palmately lobed and toothed.
*Texture of top surface.*—Lightly pubescent.
*Texture of bottom surface.*—Lightly pubescent.
*Leaf internode length.*—Approximately 3 cm.
*Color.*—Young foliage upper side: Near Green 137A. Young foliage under side: Near Green 137C. Mature foliage upper side: Near Green 137A. Mature foliage under side: Near Green 138A.
*Venation.*—Type: Palmately net. Venation color upper side: Near Yellow-green 144C. Venation color under side: Near Green 138B.

Petiole:
*Average length.*—Approximately 2.6 cm.
*Color.*—Near Green 138A.
*Diameter.*—Approximately 0.2 cm.

BLOOM

Flower:
*Flowering habit.*—Induced by darkness period greater than approximately 13.5 hours, approximately 45 days of appropriate day length required to induce and develop blooms.
*Form.*—Decorative.
*Natural flowering season.*—Approximately the first two weeks of September.
*Number of flowers per lateral branch.*—Approximately 24.
*Diameter.*—Approximately 6.8 cm.
*Depth.*—Approximately 3.2 cm.
*Longevity on plant.*—Approximately 29 days.
*Persistence.*—Persistent.

Ray florets:
*Appearance.*—Matte.
*Texture.*—Smooth.
*Average number of ray florets per flower.*—Approximately 210.
*Shape.*—Oblong.
*Aspect.*—Flat.
*Margin.*—Entire.
*Apex.*—Retuse.
*Length.*—Approximately 3.3 cm.
*Width.*—Approximately 1 cm.
*Color.*—Upper surface at first opening: Near Yellow-orange 15D. Upper surface at maturity: Near Yellow-white 158D. Upper surface at fading: Near White 155D. Under surface at first opening: Near Yellow-orange 14D. Under surface at maturity: Near Yellow-white 158D. Under surface at fading: Near White 155D.

Disc florets:
*Appearance.*—Shiny.
*Texture.*—Smooth.
*Average number of disc florets per disc.*—Approximately 10.
*Shape.*—Cylindric.
*Apex.*—Obtuse.
*Average length.*—Approximately 0.4 cm.
*Average width.*—Approximately 0.1 cm.
*Color.*—At first opening: Near Yellow-green 154D. At maturity: Near Yellow 4C. At fading: Near Yellow-orange 16B.

Peduncle:
*Length.*—At terminal end (shortest): Approximately 4.5 cm. At lateral end (longest): Approximately 7.9 cm.
*Angle to stem.*—Acute.
*Strength.*—Moderate.
*Color.*—Near Green 137A.
*Habit.*—Upright.
*Diameter.*—Approximately 0.2 cm.
*Surface texture.*—Lightly pubescent.

Flower bud:
*Length.*—Approximately 1 cm.
*Diameter.*—Approximately 0.9 cm.
*Form.*—Globular.
*Color.*—Near Yellow-orange 18C.

Involucral bracts (phyllaries):
*Appearance.*—Matte.
*Texture.*—Lightly pubescent.
*Number.*—Approximately 48.
*Shape.*—Oblanceolate.
*Margin.*—Entire.
*Apex.*—Acute.
*Length.*—Approximately 1.4 cm.
*Width.*—Approximately 0.8 cm.
*Color.*—Upper side: Near Green 137A. Under side: Near Green 138A.

REPRODUCTIVE ORGANS

Ray florets:
*Number of pistils per floret.*—1.
*Stigma shape.*—2 branched.
*Stigma color.*—Near Yellow 7A.
*Style color.*—Near Yellow 2C.
*Style length.*—Approximately 0.8 cm.
*Stamens.*—Absent.

Disc florets:

*Number of pistils per floret.*—1.
*Stigma shape.*—Two-branched.
*Stigma color.*—Near Yellow 2C.
*Style length.*—Approximately 0.3 cm.
*Style color.*—Near Yellow-green 154D.
*Number of stamens per floret.*—Approximately 5.
*Anther shape.*—Tubular.
*Anther color.*—Near Yellow 12C.
*Pollen color.*—No pollen detected.

OTHER CHARACTERISTICS

Disease resistance: Neither resistance nor susceptibility to diseases or pests has been observed in this variety.

Drought tolerance/cold tolerance: Flowering plants are hardy to a low temperature of about −2° C. Non-flowering plants are hardy in the approximate range of 3° C. to −6° C., depending upon duration of cold an amount of moisture in the soil. With adequate water plants are hardy to a high temperature of 45° C.

Fruit/seed production: Commercially, this plant is not used or observed in a stage wherein seeds would be produced. Therefore, seed production has not been observed.

What is claimed is:

1. A new and distinct cultivar of *Chrysanthemum* plant named 'Gedi Three Mil' as herein illustrated and described.

* * * * *